United States Patent [19]
Wada et al.

[11] Patent Number: 6,150,582
[45] Date of Patent: *Nov. 21, 2000

[54] ABSORBENT ARTICLE AND PRODUCTION PROCESS THEREFOR

[75] Inventors: Katsuyuki Wada; Naoko Takahashi; Hiroko Ueda; Kinya Nagasuna, all of Himeji, Japan

[73] Assignee: Nippon Shokubai Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/082,923

[22] Filed: May 21, 1998

[30] Foreign Application Priority Data

Jun. 13, 1997 [JP] Japan .................................... 9-156265

[51] Int. Cl.$^7$ .................................................. A61F 13/20
[52] U.S. Cl. ..................... 604/372; 604/358; 604/367; 604/385.1; 604/368; 604/375
[58] Field of Search ..................................... 604/375, 372, 604/358, 367, 385.1, 368

[56] References Cited

U.S. PATENT DOCUMENTS

| | | |
|---|---|---|
| 5,122,405 | 6/1995 | Dairoku et al. . |
| 5,601,542 | 2/1997 | Melius et al. . |
| 5,676,660 | 10/1997 | Mukaida et al. .................. 604/375 |
| 5,760,080 | 6/1998 | Wada et al. . |

FOREIGN PATENT DOCUMENTS

| | | |
|---|---|---|
| 0 339 461 | 11/1989 | European Pat. Off. . |
| 0 339 461 A1 | 11/1989 | European Pat. Off. . |
| 0 443 627 | 8/1991 | European Pat. Off. . |
| 0 443 627 A2 | 8/1991 | European Pat. Off. . |
| 0 532 002 | 3/1993 | European Pat. Off. . |
| 0 532 002 A1 | 3/1993 | European Pat. Off. . |
| 0 648 800 | 4/1995 | European Pat. Off. . |
| 0 668 080 | 8/1995 | European Pat. Off. . |
| 0 761 241 | 3/1997 | European Pat. Off. . |
| 0 763 364 | 3/1997 | European Pat. Off. . |
| 0 837 076 | 4/1998 | European Pat. Off. . |
| 63-99861 | 5/1988 | Japan . |

*Primary Examiner*—John G. Weiss
*Assistant Examiner*—Miley C. Peppers

[57] ABSTRACT

The invention clarifies absorption properties of a water-absorbent resin as needed in the case where the ratio by weight of the water-absorbent resin to the total of the water-absorbent resin and the fibrous material is "$\alpha$," and further the invention provides an absorbent article using a water-absorbent resin which is optimal to the ratio by weight "$\alpha$" of the water-absorbent resin. A water-absorbent resin, having a concentration absorption index of 35 or more as shown by the following equation (1):

$$A(1-\alpha)+B\alpha \qquad (1)$$

wherein A (g/g) is an absorption capacity of the resin under no load, and

B (g/g) is an absorption capacity of the resin under a load, is used as the water-absorbent resin as used for the absorbent article of at least 0.4 in the ratio by weight "$\alpha$" of the water-absorbent resin to the total of the water-absorbent resin and the fibrous material.

12 Claims, 3 Drawing Sheets

ABSORBENT ARTICLE AND PRODUCTION PROCESS THEREFOR

BACKGROUND OF THE INVENTION

A. Technical Field

The present invention relates to an absorbent article as favorably used for sanitary materials such as paper diapers (disposable diapers), sanitary napkins, and so-called incontinence pads.

B. Background Art

In recent years, water-absorbent resins are widely utilized as constituents of sanitary materials, such as paper diapers, sanitary napkins, and so-called incontinence pads, for the purpose of allowing the water-absorbent resins to absorb body fluids.

As to the above-mentioned water-absorbent resins, the following materials are, for example, known: crosslinked matters of partially neutralized polyacrylic acids, hydrolysates of starch-acrylonitrile graft polymers, neutralized products of starch-acrylic acid graft polymers, saponified products of vinyl acetate-acrylic ester copolymers, hydrolysates of acrylonitrile copolymers or those of acrylamide copolymers, or crosslinked matters of these copolymers, and crosslinked matters of cationic monomers.

It has so far been said that the above-mentioned water-absorbent resins should be excellent in the following properties: the amount of water as absorbed, the water absorption speed, the gel strength, the suction power to suck up water from a base material containing an aqueous liquid, and so on, upon contact with an aqueous liquid such as a body fluid. In addition, various water-absorbent resins or various absorbent matters or articles using the water-absorbent resins have so far been proposed, wherein the water-absorbent resins have at least two of the above-mentioned properties together and display excellent performances (water absorption properties) when used for sanitary materials such as paper diapers and sanitary napkins.

As to the above-mentioned conventional water-absorbent resins or the above-mentioned conventional absorbent matters or articles using the water-absorbent resins, the following materials are, for example, known: water-absorbent resins having a specific gel capacity, a specific shear elasticity, and an specific extractable-polymer content in combination, water-absorbent resins of which the amount of water as absorbed, the water absorption speed, and the gel strength are specified, and paper diapers or sanitary napkins using these water-absorbent resins, and paper diapers using water-absorbent resins displaying a specific amount of water as absorbed, a specific water absorption speed, and a gel stability, and water-absorbent articles using water-absorbent resins of which the amount of water as absorbed, the suction power, and the amount of water-soluble components are specified, and water-absorbent sanitary articles containing water-absorbent resins of which the amount of water as absorbed, the amount of water as absorbed under a load, and the gel fracture strength are specified (JP-A-63-099861); paper diapers containing water-absorbent resins of which the amount of water as absorbed and the water absorption speed under a load are specified, and water-absorbing agents containing water-absorbent resins of which the amount of water as absorbed under a load and the particle diameter are specified (European Patent No. 339,461); water-absorbing agents containing water-absorbent resins in not smaller than a specific amount wherein the water absorption speed and the amount of water as absorbed under a load in a short period of time are specified with regard to the water-absorbent resins (European Patent No. 443,627); water-absorbent combined materials containing water-absorbent resins in not smaller than a specific amount wherein the shape change and the suction index, both under a load, are specified with regard to the water-absorbent resins (European Patent No. 532,002); absorbent articles using resins of which the pressure absorption index and the 16-hour extractability level are regulated (European Patent No. 615,736).

In recent years, the absorbent articles such as paper diapers and sanitary napkins are advancing in high functionalization and thinning, and the amount of water-absorbent resins as used per sheet of the absorbent articles or the ratio by weight of water-absorbent resins to the total of the water-absorbent resins and fibrous materials tends to increase. In other words, attempts are made to increase the ratio of water-absorbent resins in absorbent matters by lessening fibrous materials with a small bulk density and increasing the water-absorbent resins with excellent water absorbency and a large bulk density, and to thereby thin the sanitary materials without lowering the amount of water as absorbed.

At present, there is not yet any clear answer to problems about what property is most necessary to the above-mentioned water-absorbent resins for increasing the absorption amount of absorbent articles in practical use when producing absorbent articles containing a relatively large amount of water-absorbent resins, in other words, for producing absorbent articles which merely involve leakage as little as possible.

In addition, there is not any clear answer, either, to problems about that how to change properties of water-absorbent resins, as used, for the purpose of increasing or keeping the absorption amount of absorbent articles as final products when changing the resin ratio (the ratio by weight of water-absorbent resins to the total of the water-absorbent resins and fibrous materials) in absorbent matters is preferable in technical and economical respects.

In addition, there are also problems in that: performances of absorbent articles containing a relatively large amount of water-absorbent resins greatly depend on the water-absorbent resins, and the absorption amount of the absorbent articles is easily influenced by property differences of water-absorbent resins, as used, between makers thereof, and by performance variations of water-absorbent resins as used, and further by resin ratio variations and so on.

Thus, there is not yet any solution to problems about what properties of water-absorbent resins should be noted and how such properties should be modified, in response to the change or variation of the resin ratio, for the purpose of allowing absorbent articles such as paper diapers and sanitary napkins to display their objective performances maximally and stably in each state in the case where the resin ratios in absorbent matters are different and for the purpose of preventing differences in performance of the absorbent articles, or otherwise how to change the resin ratio in response to differences or variations of properties of the water-absorbent resins.

SUMMARY OF THE INVENTION

A. Objects of the Invention

Objects of the present invention are to clarify absorption properties of a water-absorbent resin as needed in the case where the resin ratio is a specific value, and to provide an absorbent article using a water-absorbent resin which is optimal to each resin ratio of the water-absorbent resin, with the absorbent article displaying not only a constantly stable and high absorption amount, but also a high absorption amount until the leakage occurs in the use form very near to practical use, and further to provide a process for producing the absorbent article.

B. Disclosure of the Invention

The present inventors diligently studied about relations between the resin ratio in absorbent matters and properties of water-absorbent resins to achieve the above-mentioned objects, and as a result, completed the present invention by finding that the absorption amount, as displayed until the leakage occurs in the use form very near to practical use of an absorbent article, depends upon a specific relation as led from two properties of absorption capacities of the water-absorbent resin under no load and under a specific load and from the resin ratio in absorbent matters, and that if the water-absorbent resin or the resin ratio is selected so as to enlarge the value of an equation of the above-mentioned relation, the absorption amount in the use form very near to practical use of the absorbent article increases, and further that if only the value of an equation of the above-mentioned relation is equal even between different kinds of water-absorbent resins, the absorption amounts in the use form very near to practical use of the resultant absorbent articles, as displayed until the leakage occurs, can be designed to be the same.

Thus, the present invention relates to a process for producing an absorbent article having an absorbent layer, a liquid-permeable surface sheet, and a liquid-impermeable back sheet, wherein the absorbent layer includes an absorbent matter having a water-absorbent resin and a fibrous material in a ratio by weight, "α," of the water-absorbent resin to the total of the water-absorbent resin and the fibrous material, wherein the ratio by weight "α" is at least 0.4, with the process comprising the step of using as the water-absorbent resin a water-absorbent resin which has a concentration absorption index of 35 or more as shown by the following equation (1):

$$A(1-\alpha)+B\alpha \tag{1}$$

wherein A (g/g) is an absorption capacity of the resin under no load, and

B (g/g) is an absorption capacity of the resin under a load.

The present invention further relates to an absorbent article comprising an absorbent layer, a liquid-permeable surface sheet, and a liquid-impermeable back sheet, wherein the absorbent layer includes an absorbent matter having a water-absorbent resin and a fibrous material in a ratio by weight, "α," of the water-absorbent resin to the total of the water-absorbent resin and the fibrous material, wherein the ratio by weight "α" is at least 0.4, and wherein the water-absorbent resin has a concentration absorption index of 35 or more as shown by the following equation (1):

$$A(1-\alpha)+B\alpha \tag{1}$$

wherein A (g/g) is an absorption capacity of the resin under no load, and

B (g/g) is an absorption capacity of the resin under a load.

These and other objects and the advantages of the present invention will be more fully apparent from the following detailed disclosure.

DETAILED DESCRIPTION OF THE INVENTION

Figure 1:
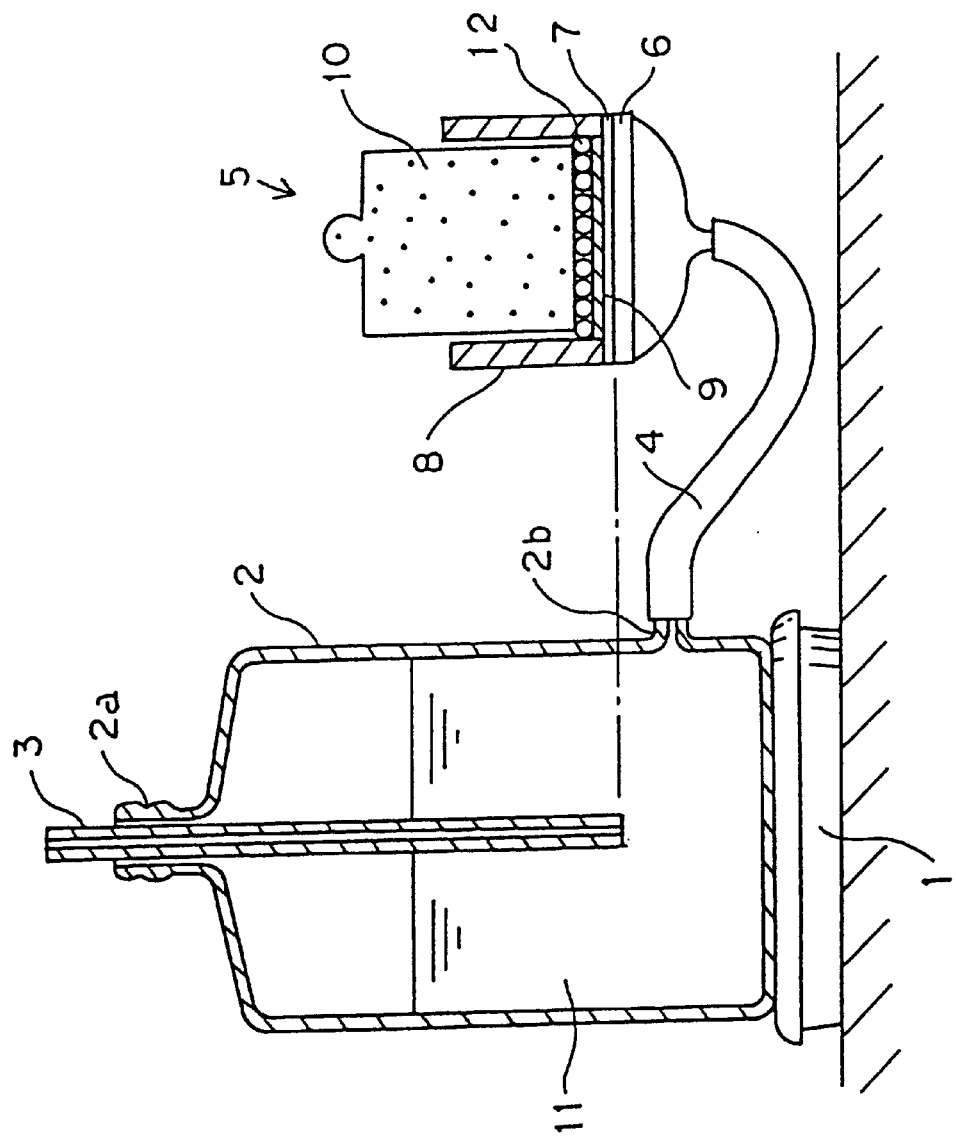
FIG. 1 is a schematic section of a measurement apparatus as used for measuring the absorption capacity under a load, which is one of properties that the water-absorbent resin displays.

Hereinafter, the present invention is explained in detail.

The concentration absorption index in the present invention is a sum of values as given by multiplying absorption capacities of the water-absorbent resin under no load and under a load, respectively, by specific ratios as determined from the ratio by weight "α" of the water-absorbent resin to the total of the water-absorbent resin and the fibrous material.

Selection of not only the ratio by weight "α" of a water-absorbent resin to the total of the water-absorbent resin and a fibrous material, but also the water-absorbent resin, so as to meet the above-mentioned equation relation, could improve the absorption amount in a state near to practical use of the resultant absorbent article. Furthermore, selection of water-absorbent resins with values of the absorption capacity (A) under no load and values of the absorption capacity (B) under a load to give an equal concentration absorption index between the water-absorbent resins could provide absorbent articles which display almost the same absorption amount in a state near to practical use even if the value of the absorption capacity (A) under no load and the value of the absorption capacity (B) under a load are different between the water-absorbent resins. In addition, the absorption capacity under a load herein needs to be a value as measured under a load of 50 (g/cm$^2$) using a specific artificial urine as illustrated by the below-mentioned examples of some preferred embodiments.

Many of the above-mentioned prior art documents on patent applications evaluate only the absorption capacity under a load. Conditions for measuring the absorption capacity under a load, as have so far been proposed, are 20 (g/cm$^2$), 50 (g/cm$^2$), and so on, but absorption properties of the absorbent article according to the present invention cannot be predicted from a relatively low condition value of 20 (g/cm$^2$). Furthermore, the present inventors hereby clarified that the significance of the absorption properties of the absorbent article according to the present invention varies with the ratio by weight "α" of the water-absorbent resin to the total of the water-absorbent resin and the fibrous material. Specifically, even if only the value of the absorption capacity under a load is sought, the absorption amount in a state near to practical use of absorbent articles such as paper diapers containing fibrous materials cannot be improved, and such an improvement needs selection of such a resin as has a concentration absorption index falling in the scope of the present invention.

The absorbent article of the present invention contains the absorbent matter having a ratio by weight, "α," of the water-absorbent resin to the total of the water-absorbent resin and the fibrous material. In the case where α is small, the absorption capacity (A) under no load tends to be taken more seriously with regard to usable water-absorbent resins, but a resin having a high absorption capacity under a load is also available if the concentration absorption index is considered. In addition, in the case where α is large, the significance of the absorption capacity (B) under a load tends to increase with regard to usable water-absorbent resins, but a resin having a high absorption capacity (A) under no load is also available if the concentration absorption index is considered. For allowing effects of the present invention to greatly emerge, α needs to be at least 0.4, and is preferably in the range of 0.5 to 0.9, more preferably, 0.6 to 0.9, particularly preferably, 0.6 to 0.8. In the case where α is less than 0.4, property differences of water-absorbent resins might not greatly be exhibited as performance differences of absorbent articles, depending upon the types of the water-absorbent resins. In addition, in the case where α is more than 0.9, the resin and the fibrous material might be difficult to mix together. In addition, the absorption capacity (A) under no load and the absorption capacity (B) under a load herein, as needed for determining the value of the concentration absorption index, are defined with values thereof as measured a predetermined time after the initiation of the absorption in the below-mentioned measurement under a load of 50 (g/cm$^2$). Herein, the absorption capacity (A) under no load is preferably 30 (g/g) or more, and the absorption capacity (B) under a load is preferably 10 (g/g) or more.

In addition, examples of other absorption properties of water-absorbent resins include the stability of a swollen gel to urine (urine resistance), the moderate water absorption speed as derived from the particle diameter or specific surface area of resin particles, and the liquid permeability between gel layers. If these properties are improved, the absorption amount in a state near to practical use of absorbent articles might be further improved. Particularly, it should be noted that in the case where the stability of a swollen gel to urine is low, the absorption amount of absorbent articles might be smaller than expected ones. The water-absorbent resin has a urine resistance index of, preferably, 10 or less, more preferably, 1 or less, as measured in the below-mentioned manner. In addition, a preferable average particle diameter of a water-absorbent resin as used is 500 μm or less considering initial dry feeing and so on of absorbent articles.

In the present invention, the ratio by weight "α" of the water-absorbent resin to the total of the water-absorbent resin and the fibrous material is determined such that the concentration absorption index of the equation (1) may be 35 (g/g) or more. In the case where the concentration absorption index is less than 35 (g/g), the absorption amount in a state near to practical use of the resultant absorbent article is small and, for example, in the case where the absorbent article is a paper diaper, there is a high possibility that the leakage might occur. The concentration absorption index is preferably not less than 37 (g/g), more preferably, not less than 40 (g/g), most preferably, not less than 45 (g/g).

The absorption amount in a state near to practical use of the absorbent article can be predicted with the concentration absorption index as defined in the present invention, but if the liquid permeation speed of the absorbent matter is regulated so as to fall in a specific range, the prediction more exactly can be made, wherein the liquid permeation speed of the absorbent matter is a speed (liquid permeation speed) at which a fluid passes through inside the absorbent matter. As is illustrated by the below-mentioned examples of some preferred embodiments, when a certain amount of physiological salt solution is injected into the absorbent matter thrice in total at a certain interval of time under a load of 20 g/cm$^2$, a measured value (g/min) of the amount per unit time of the physiological salt solution as flows out due to the second injection is defined as a "second-time liquid permeation speed of the absorbent matter," and a measured value (g/min) of the amount per unit time of the physiological salt solution as flows out due to the third injection is defined as a "third-time liquid permeation speed of the absorbent matter." The "second-time liquid permeation speed of the absorbent matter" is well correlative with a liquid permeation speed of the absorbent article in a state where the swelling capacity of the water-absorbent resin is low, and the "third-time liquid permeation speed of the absorbent matter" is well correlative with a liquid permeation speed of the absorbent article in a state where the swelling capacity of the water-absorbent resin is high.

In the case where a liquid passes through inside the absorbent matter in a short time, the water-absorbent resin might not be able to fully absorb the liquid, and the resultant absorption amount might be small. Thus, it might be unfavorable that the liquid permeation speed of the absorbent matter is too high in a state where the swelling capacity of the water-absorbent resin is low. Thus, the present inventors diligently studied about the liquid permeation speed, and as a result, found that there is a relation between the liquid permeation speed of the fibrous material, as used, and the ratio of the fibrous material as used in the absorbent matter, and that the "second-time liquid permeation speed of the absorbent matter" is preferably at most $\gamma$ (1−α) (g/min), wherein $\gamma$ (g/min) is a liquid permeation speed of the fibrous material. What this boils down to is that the liquid permeation speed of the absorbent matter depends upon the resin ratio and is not higher than the liquid permeation speed of the fibrous material proportional to the ratio of the fibrous material as used in the absorbent matter.

On the other hand, in the case where the liquid permeation speed in the absorbent matter is too low, the liquid cannot permeate the absorbent matter, or even if the liquid does permeate the absorbent matter, the permeated liquid might hardly diffuse, so the water-absorbent resin might be hindered from efficiently absorbing the liquid. Thus, it is unfavorable that the liquid permeation speed of the absorbent matter is too low, especially, in a state where the swelling capacity of the water-absorbent resin is high. The "third-time liquid permeation speed of the absorbent matter" is preferably at least 0.05 (g/min), more preferably, at least 0.10 (g/min).

In the measurement of the second-time liquid permeation speed of the absorbent matter, the liquid might not flow out because of absorption of the entire liquid by the absorbent matter, but, in the case where the liquid passes through the absorbent matter, the "second-time liquid permeation speed of the absorbent matter" is also preferably at least 0.05 (g/min), more preferably, at least 0.10 (g/min).

In addition, even if the concentration absorption index is 35 (g/g) or more, it is preferable that the amount of the water-absorbent resin as used is 8 g or larger. An absorbent article having the water-absorbent resin as used in an amount smaller than 8 g might lack dry feeling as a product and might involve a very large amount of desorption. The amount of the water-absorbent resin as used is more preferably in the range of 10–20 (g/g). In addition, the weight of the water-absorbent resin in the absorbent matter is preferably 100 (g/m$^2$) or more.

The absorbent matter in the absorbent article of the present invention, in general, further comprises a fibrous material such as a hydrophilic fiber in addition to the water-absorbent resin. In the case where the absorbent matter, for example, comprises the water-absorbent resin and the hydrophilic fiber, a constitution of the absorbent matter comprising a homogeneous mixture of the water-absorbent resin and the hydrophilic fiber is, for example, preferable for sufficiently displaying effects of the present invention. Examples of such a constitution include: a constitution comprising a homogeneous mixture of the water-absorbent resin and the hydrophilic fiber; a constitution comprising a layer of a homogeneous mixture of the water-absorbent resin and the hydrophilic fiber and a layer of the hydrophilic fiber as laminated on the preceding layer; a constitution comprising a layer of a homogeneous mixture of the water-absorbent resin and the hydrophilic fiber, a layer of the hydrophilic fiber, and the water-absorbent resin as interposed between these layers; and further a constitution comprising the water-absorbent resin as interposed between layers of the hydrophilic fiber; and still further a constitution comprising a sheet of the water-absorbent resin as shaped by combining a specific amount of water with the water-absorbent resin. Incidentally, the constitution of the absorbent matter is not limited to the above-mentioned examples thereof.

Examples of the above-mentioned fibrous material include hydrophilic fibers such as: cellulose fibers, for example, mechanical pulp, chemical pulp, semichemical pulp, digested pulp, as obtained from wood; and artificial cellulose fibers, for example, rayon, acetates. Among the above-exemplified fibers, cellulose fibers are preferable. In addition, the hydrophilic fibers may comprise synthetic fibers such as polyamides, polyesters, and polyolefins. Incidentally, the fibrous material is not limited to the above-exemplified fibers.

In addition, in the case where the ratio of the fibrous material such as the hydrophilic fiber in the absorbent matter is relatively small, the absorbent matters, namely, the hydrophilic fibers, may be allowed to adhere together using adhesive binders. If the hydrophilic fibers are allowed to adhere together, the strength and the shape retainability of the absorbent matter before or during the use thereof can be enhanced.

Examples of the above-mentioned adhesive binders include: heat-sealable fibers such as polyolefin fibers (e.g., polyethylene, polypropylene, ethylene-propylene copolymers, 1-butene-ethylene copolymers); and adhesive emulsions. These adhesive binders may be used either alone or in combinations of at least two thereof. The ratio by weight of the hydrophilic fiber and the adhesive binder is preferably in the range of 50/50 to 99/1, more preferably, 70/30 to 95/5, still more preferably, 80/20 to 95/5.

In addition, as to the absorbent article of the present invention, an absorbent layer comprising the above-mentioned absorbent matter is interposed between a liquid-permeable surface sheet and a liquid-impermeable back sheet, but it is permissible that a diffusion layer for helping a liquid diffuse, comprising nonwoven fabrics, cellulose, or crosslinked cellulose, is put on an upper face of the absorbent layer or a back or upper face of the surface sheet.

The water-absorbent resin, usable in the present invention, has a concentration absorption index of 35 or more as shown by the following equation (1):

$$A(1-\alpha)+B\alpha \qquad (1)$$

wherein A (g/g) is an absorption capacity of the resin under no load,

B (g/g) is an absorption capacity of the resin under a load, and $\alpha$ is a ratio by weight of the water-absorbent resin to the total of the water-absorbent resin and the fibrous material.

Such a water-absorbent resin can generally be obtained by a production process comprising the step of subjecting a water-absorbent resin precursor to a surface-crosslinking treatment. The above-mentioned water-absorbent resin precursor is a resin with a carboxyl group, which has an average particle diameter in the range of, preferably, 100 to 600 $\mu$m, more preferably, 100 to 400 $\mu$m, and a proportion of particles, with a particle diameter less than 106 $\mu$m, of not more than 10% by weight, and most preferably, as disclosed in JP-B-06-025209, a logarithmic standard deviation, $\sigma_g$, of a particle diameter distribution of 0.35 or less, and which is formable into a hydrogel upon absorbing a large amount of water.

The above-mentioned water-absorbent resin precursor is, for example, synthesized by aqueous solution polymerization or reversed-phase suspension polymerization. Specific examples of the water-absorbent resin precursor include: crosslinked matters of partially neutralized polyacrylic acids, hydrolysates of starch-acrylonitrile graft polymers, neutralized products of starch-acrylic acid graft polymers, saponified products of vinyl acetate-acrylic ester copolymers, hydrolysates of acrylonitrile copolymers or those of acrylamide copolymers, or crosslinked matters of these copolymers, and denatured products of carboxyl group-containing crosslinked polyvinyl alcohols, and crosslinked isobutylene-maleic anhydride copolymers.

The above-mentioned water-absorbent resin precursor, for example, can be obtained by polymerizing or copolymerizing at lease one monomer selected from the group consisting of unsaturated carboxylic acids, such as (meth) acrylic acid, maleic acid, maleic anhydride, fumaric acid, crotonic acid, itaconic acid, and $\beta$-acryloyloxypropionic acid, and neutralized products thereof, and then, in case of need, pulverizing and classifying the resultant polymer to regulate it into the above-mentioned average particle diameter. Among the above-mentioned monomers, (meth)acrylic acid and neutralized products thereof are preferable.

Furthermore, the above-mentioned water-absorbent resin precursor may be a copolymer of the above-mentioned monomer and another monomer copolymerizable therewith. Specific examples of the other monomer include: anionic unsaturated monomers, such as vinylsulfonic acid, styrenesulfonic acid, 2-(meth)acrylamido-2-methylpropanesulfonic acid, 2-(meth)acryloylethanesulfonic acid, and 2-(meth) acryloylpropanesulfonic acid, and salts thereof; nonionic hydrophilic group-containing unsaturated monomers such as acrylamide, methacrylamide, N-ethyl(meth)acrylamide, N-n-propyl(meth)acrylamide, N-isopropyl(meth) acrylamide, N,N-dimethyl(meth)acrylamide, 2-hydroxyethyl (meth)acrylate, 2-hydroxypropyl (meth) acrylate, methoxypolyethylene glycol (meth)acrylate, polyethylene glycol mono(meth)acrylate, vinylpyridine, N-vinylpyrrolidone, N-acryloylpiperidine, and N-acryloylpyrrolidine; cationic unsaturated monomers, such as N,N-dimethylaminoethyl (meth)acrylate, N,N-diethylaminoethyl (meth)acrylate, N,N-dimethylaminopropyl (meth)acrylate, and N,N-dimethylaminopropyl(meth)acrylamide, and quaternary salts thereof.

The carboxyl group content in the water-absorbent resin precursor is not especially limited, but is preferably in the range of 0.01 equivalents or more per 100 g of the water-absorbent resin precursor. In addition, in the case where the water-absorbent resin precursor is, for example, the crosslinked matter of partially neutralized polyacrylic acid, the ratio of unneutralized polyacrylic acid in this crosslinked matter is desirably in the range of 1 to 60 mol %, more desirably, 10 to 50 mol %.

It is preferable that the water-absorbent resin precursor is such as internally crosslinked by a reaction or copolymerization with a crosslinking agent having at least two polymerizable unsaturated groups or at least two reactive groups. In addition, the water-absorbent resin precursor may be a self-crosslinking type which does not need any crosslinking agent. Specific examples of the crosslinking agent include N,N'-methylenebis(meth)acrylamide, (poly)ethylene glycol di(meth)acrylate, (poly)propylene glycol di(meth)acrylate, trimethylolpropane di(meth)acrylate, trimethylolpropane tri(meth)acrylate, glycerol tri(meth)acrylate, glycerol acrylate methacrylate, ethylene oxide-denatured trimethylolpropane tri(meth)acrylate pentaerythritol tetra(meth)acrylate, dipentaerythritol hexa(meth)acrylate, triallyl cyanurate, triallyl isocyanurate, triallyl phosphate, triallylamine, poly(meth) allyloxyalkanes, (poly)ethylene glycol diglycidyl ether, glycerol diglycidyl ether, ethylene glycol, polyethylene glycol, propylene glycol, glycerol, pentaerythritol, ethylenediamine, polyethylenimine, and glycidyl (meth) acrylate. These crosslinking agents may be used either alone or in combinations of at least two thereof. Among the above-exemplified compounds, compounds with at least two polymerizable unsaturated groups are preferably used as the crosslinking agents.

The amount of the crosslinking agent as used is preferably in the range of 0.005 to 2 mol %, more preferably, 0.05 to 1 mol %, of the total of the above-mentioned monomers. In the case where the amount of the crosslinking agent as used is smaller than 0.005 mol %, the stability of a swollen gel of the water-absorbent resin to urine might unfavorably be deteriorated.

In addition, when the polymerization is initiated in the above-mentioned polymerization reaction, the following, for example, can be used: radical polymerization initiators such as potassium persulfate, ammonium persulfate, sodium persulfate, t-butyl hydroperoxide, hydrogen peroxide, and 2,2'-azobis(2-amidinopropane) dihydrochloride; or active energy rays such as ultraviolet rays and electron rays. In addition, when oxidizable radical polymerization initiators are used, redox polymerization can, for example, be carried out using jointly therewith reductants such as sodium sulfite, sodium hydrogen sulfite, ferrous sulfate, and L-ascorbic acid. The amount of these polymerization initiators as used is preferably in the range of 0.001 to 2 mol %, more preferably, 0.01 to 0.5 mol %, of the total of the above-mentioned monomers.

The above-mentioned water-absorbent resin precursor does generally not fall in the preferable range of the absorption capacity (B) under a load in the present invention, so the crosslinking density in the surface neighborhood of the water-absorbent resin precursor needs to be increased to a higher value than that inside the water-absorbent resin precursor using a specific surface-crosslinking agent. Thus, the water-absorbent resin, usable in the present invention, is obtained by crosslinking the surface neighborhood of the water-absorbent resin precursor using the specific surface-crosslinking agent.

Thus, the water-absorbent resin, usable in the present invention, is obtained by regulating the above-mentioned water-absorbent resin precursor, as preferably obtained by the foregoing aqueous solution polymerization, by operations such as classification so as to have an average particle diameter of 100 to 600 µm, preferably, 100 to 400 µm, and a proportion of particles, with a particle diameter less than 106 µm, of not more than 10% by weight, and more preferably, as disclosed in JP-B-06-025209, a logarithmic standard deviation, $\sigma_g$, of a particle diameter distribution of 0.35 or less, and then thermally treating the water-absorbent resin precursor in the presence of the specific surface-crosslinking agent.

The above-mentioned water-absorbent resin precursor may be granulated into a predetermined shape and can have various shapes such as spheres, scales, formless pulverized shapes, and granules. Furthermore, the water-absorbent resin precursor may comprise either primary particles or a granulated matter thereof. Incidentally, with regard to the water-absorbent resin precursor, in the case where the average particle diameter is out of the range of 100 to 600 µm or where the proportion of particles with a particle diameter less than 106 µm is more than 10% by weight, it might be impossible to obtain the water-absorbent resin with an excellent concentration absorption index.

The above-mentioned surface-crosslinking agent is not especially limited, and conventional ones can be used. However, it is preferable to jointly use a first and a second surface-crosslinking agent which have solubility parameters (SP values) different from each other, because the permeation of these crosslinking agents into the water-absorbent resin surface is easy to optionally select along with the crosslinking thickness, and because a water-absorbent resin having an especially excellent absorption capacity (B) under a load is therefore easy to obtain, and because the present invention resin with an excellent concentration absorption index is therefore easy to obtain. Incidentally, the above-mentioned solubility parameter is a value as commonly used as a factor showing the polarity of compounds. Values of solubility parameters, $\sigma$ $(cal/cm^3)^{1/2}$, of solvents, as disclosed on pages 527–539 of *Polymer Handbook*, 3rd edition, published by WILEY INTERSCIENCE, are applied to the above-mentioned solubility parameter in the present invention. In addition, values, as applied to solubility parameters of solvents as not disclosed on the above-mentioned pages, are led by substituting Hoy's cohesive energy constant, as disclosed on page 525 of the *Polymer Handbook* above, for Small's equation as disclosed on page 524 of the *Polymer Handbook* above.

The above-mentioned first surface-crosslinking agent is preferably a compound which is reactive upon a carboxyl group and has a solubility parameter of 12.5 $(cal/cm^3)^{1/2}$ or more, further preferably, 13.0 $(cal/cm^3)^{1/2}$ or more. Examples of the first surface-crosslinking agent include ethylene glycol, propylene glycol, glycerol, pentaerythritol, sorbitol, ethylene carbonate (1,3-dioxolan-2-one), propylene carbonate (4-methyl-1,3-dioxolan-2-one), but the first surface-crosslinking agent is not limited to these compounds. These first surface-crosslinking agents may be used either alone or in combinations of at least two thereof.

The above-mentioned second surface-crosslinking agent is preferably a compound which is reactive upon a carboxyl group and has a solubility parameter less than 12.5 $(cal/cm^3)^{1/2}$, more preferably, in the range of 9.5 to 12.0 $(cal/cm^3)^{1/2}$. Examples of the second surface-crosslinking agent include diethylene glycol, triethylene glycol, tetraethylene glycol, dipropylene glycol, tripropylene glycol, 1,3-propanediol, 1,4-butanediol, 1,5-pentanediol, 2,4-pentanediol, 1,6-hexanediol, 2,5-hexanediol, trimethylolpropane, diethanolamine, triethanolamine, ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, ethylenediamine, diethylenetriamine, triethylenetetramine, 2,4-tolylene diisocyanate, hexamethylene diisocyanate, 4,5-dimethyl-1,3-dioxolan-2-one, epichlorohydrin, epibromohydrin, but the second surface-crosslinking agent is not limited to these compounds. These second surface-crosslinking agents may be used either alone or in combinations of at least two thereof.

The amount of the surface-crosslinking agent as used depends upon the compounds as used as such, or on combinations thereof, but is preferably in the range of 0.01 to 5 parts by weight of the first surface-crosslinking agent and 0.001 to 1 part by weight of the second surface-crosslinking agent, and more preferably in the range of 0.1 to 2 parts by weight of the first surface-crosslinking agent and 0.005 to 0.5 parts by weight of the second surface-crosslinking agent, relative to 100 parts by weight of the solid content of the water-absorbent resin precursor. If the above-mentioned surface-crosslinking agents are used, the crosslinking density in the surface neighborhood of the water-absorbent resin precursor, namely, the water-absorbent resin, can be increased to a higher value than that inside, whereby the absorption capacity (B) under a load as needed for the present invention resin can be enhanced. The amount of the surface-crosslinking agent, as used, larger than 10 parts by weight is unfavorable because it is not only uneconomical, but also is excessive to the formation of the optimal crosslinking structure in the water-absorbent resin and therefore lowers the absorption capacity (A) under no load. In addition, in the case where the amount of the surface-crosslinking agent as used is smaller than 0.001 parts by weight, effects for improving the absorption capacity (B) under a load in the water-absorbent resin is unfavorably difficult to obtain.

When the water-absorbent resin precursor and the surface-crosslinking agent are mixed together, water is preferably used as the solvent. The amount of water as used depends upon the type or particle diameter of the water-absorbent resin precursor, but is preferably in the range of 0 to 20 parts by weight (but not including 0 parts by weight), and preferably in the range of 0.5 to 10 parts by weight, relative to 100 parts by weight of the solid content of the water-absorbent resin precursor.

In addition, when the water-absorbent resin precursor and the surface-crosslinking agent are mixed together, a hydrophilic organic solvent may be used as the solvent, if necessary. Examples of the hydrophilic organic solvent include: lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane and tetrahydrofuran; amides such as N,N-dimethylformamide; and sulfoxides such as dimethyl sulfoxide. The amount of the hydrophilic organic solvent as used depends upon the type or particle diameter of the water-absorbent resin precursor, but is preferably in the range of 20 parts by weight or less, more preferably, 0.1 to 10 parts by weight, relative to 100 parts by weight of the solid content of the water-absorbent resin precursor.

In addition, when the water-absorbent resin precursor and the surface-crosslinking agent are mixed together, the water-absorbent resin precursor may, for example, be dispersed into the above-mentioned hydrophilic organic solvent, and then the surface-crosslinking agent may be mixed therewith, but the mixing method is not especially limited. Among various mixing methods, preferred is a method in which the surface-crosslinking agent, as dissolved in either or both of water and the hydrophilic organic solvent if necessary, is directly sprayed or dropped onto the water-absorbent resin precursor, thus mixing them. In addition, in the case where the mixing is made using water, water-insoluble fine particle powders or surfactants may be allowed to coexist.

A mixing apparatus, as used to mix the water-absorbent resin precursor and the surface-crosslinking agent, preferably has great mixing power to homogeneously and surely mix them. Preferable examples of the mixing apparatus include cylinder type mixers, double-wall cone type mixers, V-character-shaped mixers, ribbon type mixers, screw type mixers, fluidized-furnace rotary disk type mixers, gas current type mixers, double-arm type kneaders, internal mixers, pulverizing type kneaders, rotary mixers, screw type extruders.

After mixing the water-absorbent resin precursor and the surface-crosslinking agent, a thermal treatment is carried out to crosslink the surface neighborhood of the water-absorbent resin precursor. The treatment temperature in the thermal treatment depends upon the surface-crosslinking agent as used, but is preferably in the range of 160 to 250° C. In the case where the treatment temperature is lower than 160° C., no uniform crosslinking structure is formed and the water-absorbent resin with excellent abilities such as diffusion absorption capacity therefore cannot be obtained. In the case where the treatment temperature is higher than 250° C., the water-absorbent resin precursor is degraded and the abilities of the water-absorbent resin is therefore deteriorated.

The above-mentioned thermal treatment can be carried out using conventional driers or heating furnaces. Examples of the driers include thin type mixing driers, rotary driers, desk driers, fluidized-bed driers, gas current type driers, infrared driers.

The water-absorbent resin, as obtained by the above-mentioned production process, has an absorption capacity (A) under no load in the range of, generally, 30 (g/g) or more and an absorption capacity (B) under a load in the range of, generally, 10 (g/g) or more, preferably, 20 (g/g) or more, and if the balance between the two properties of the absorption capacity (A) under no load and the absorption capacity (B) under a load in the above-mentioned ranges, as well as the ratio by weight "α" of the objective water-absorbent resin to the total of the water-absorbent resin and the fibrous material, is considered to select the resin such that the value of the concentration absorption index in the present invention can be 35 (g/g) or more, the absorbent article displaying an excellent absorption amount in a state near to practical use can be obtained. In the present invention, even if there are resins of which the two properties of the absorption capacity (A) under no load and the absorption capacity (B) under a load are different between the resins, the absorption amounts in a state near to practical use of the resultant absorbent articles can almost be equalized by equalizing the values of the concentration absorption index between the resins. Accordingly, even in the case where there are property differences of water-absorbent resins, as used, between makers thereof or where there are performance variations of water-absorbent resins as used, absorbent articles of definite quality can be provided.

In addition, the absorbent article of the present invention comprises an absorbent layer which includes an absorbent matter of the above-mentioned constitution and is interposed between a sheet with liquid permeability and a sheet with liquid impermeability. Thus, because the absorbent article comprises an absorbent layer including an absorbent matter of the above-mentioned constitution, the absorbent article has the above-mentioned excellent water absorption properties. Specifically, examples of the use form of the absorbent article include sanitary materials such as paper diapers, sanitary napkins, and so-called incontinence pads, but the use form of the absorbent article is not especially limited. Because the absorbent article has excellent water absorption properties, it can prevent urine from leaking and can afford so-called dry feeling in the case where the absorbent article is, for example, a paper diaper.

The above-mentioned sheet with liquid permeability (hereinafter referred to as liquid-permeable sheet) comprises a material that is permeable with aqueous liquids. Examples of the material forming the liquid-permeable sheet include: nonwoven fabrics, woven fabrics; porous synthetic resin films of polyethylene, polypropylene, polyester, polyamide. The above-mentioned sheet with liquid impermeability (hereinafter referred to as liquid-impermeable sheet) comprises a material that is impermeable with aqueous liquids. Examples of the material forming the liquid-impermeable sheet include: synthetic resin films of polyethylene, polypropylene, ethylene vinyl acetate, polyvinyl chloride; films of combined materials of these synthetic resins with nonwoven fabrics; films of combined materials of the above-mentioned synthetic resins with woven fabrics. Incidentally, the liquid-impermeable sheet may be permeable with steam.

The constitution of the absorbent layer is not especially limited if it has the above-mentioned absorbent matter. In addition, the process for producing the absorbent layer is not especially limited. Furthermore, the method for interposing the absorbent layer between the liquid-permeable sheet and the liquid-impermeable sheet, namely, the process for producing the absorbent article, is not especially limited.

In addition, it is permissible to afford various functions to the absorbent matter or article by further adding materials such as deodorants, antibacterial agents, perfumes, various inorganic powders, foaming agents, pigments, dyes, hydrophilic short fibers, fertilizers, oxidants, reductants, water, and salts to the above-mentioned absorbent matter.

Effects and Advantages of the Invention

As is mentioned above, the absorbent article according to the present invention can display a very high absorption amount in a state very near to practical use thereof. In addition, this absorbent article can constantly retain a very high water-absorption amount, because, as to this absorbent article, a water-absorbent resin having optimal properties can easily be selected in response to variations of the ratio by weight "α" of the water-absorbent resin to the total of the water-absorbent resin and the fibrous material. Examples of the above-mentioned absorbent article include sanitary materials, such as paper diapers, sanitary napkins, and so-called incontinence pads, of which the high functionalization and the thinning are desired, and the absorbent article can particularly favorably be used for these materials.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited to these examples. Incidentally, the performances of the water-absorbent resin were measured by the following methods:

(a) Absorption Capacity Under No Load:

First, 0.2 g of water-absorbent resin was uniformly placed into a nonwoven fabric-made bag (60 mm×60 mm) and then immersed into an artificial urine (composition: an aqueous solution containing sodium sulfate of 0.2 wt %, potassium chloride of 0.2 wt %, magnesium chloride hexahydrate of 0.05 wt %, calcium chloride dihydrate of 0.025 wt %, ammonium dihydrogen phosphate of 0.085 wt %, and diammonium hydrogen phosphate of 0.015 wt %). Sixty minutes later, the bag was drawn up and then drained at 250 G for 3 minutes with a centrifuge, and the weight $W_1$ (g) of the bag was then measured. On the other hand, the same procedure was carried out using no water-absorbent resin, and the resultant weight $W_0$ (g) was measured. Thus, the absorption capacity (g/g) under no load was calculated from these weights $W_1$ and $W_0$ in accordance with the following equation:

absorption capacity (g/g) under no load=(weight $W_1$(g)−weight $W_0$(g))/(weight (g) of water-absorbent resin).

(b) Absorption Capacity Under Load:

Hereinafter, first, a measurement apparatus as used for measuring the absorption capacity under a load is simply explained while referring to FIG. 1.

As is shown in FIG. 1, the measurement apparatus comprises: a scale 1; a vessel 2 of a predetermined capacity as mounted on the scale 1; an air-inhaling pipe 3; an introducing tube 4; a glass filter 6; and a measurement part 5 as mounted on the glass filter 6. The vessel 2 has an opening part 2a on the top and an opening part 2b on the side. The air-inhaling pipe 3 is inserted in the opening part 2a, and the introducing tube 4 is fitted to the opening part 2b. In addition, the vessel 2 contains a predetermined amount of artificial urine 11 (composition: an aqueous solution containing sodium sulfate of 0.2 wt %, potassium chloride of 0.2 wt %, magnesium chloride hexahydrate of 0.05 wt %, calcium chloride dihydrate of 0.025 wt %, ammonium dihydrogen phosphate of 0.085 wt %, and diammonium hydrogen phosphate of 0.015 wt %). The lower part of the air-inhaling pipe 3 is submerged in the artificial urine 11. The glass filter 6 is formed in a diameter of 70 mm. The vessel 2 and the glass filter 6 are connected to each other through the introducing tube 4. In addition, the upper part of the glass filter 6 is fixed so as to be located a little higher than the lower end of the air-inhaling pipe 3.

The measurement part 5 comprises: a filter paper 7; a supporting cylinder 8; a wire net 9 as attached to the bottom of the supporting cylinder 8; and a weight 10; and the measurement part 5 is formed by mounting the filter paper 7 and the supporting cylinder 8 (i.e. wire net 9) in this order on the glass filter 6 and further mounting the weight 10 inside the supporting cylinder 8, namely, on the wire net 9. The supporting cylinder 8 is formed in an inner diameter of 60 mm. The wire net 9 is made of stainless steel and formed in 400 mesh (mesh size: 38 μm). An arrangement is made such that a predetermined amount of water-absorbent resin 12 can uniformly be spread on the wire net 9. The weight 10 is adjusted in weight such that a load of 50 g/cm² can uniformly be applied to the wire net 9, namely, to the water-absorbent resin 12.

The absorption capacity under a load was measured with the measurement apparatus having the above-mentioned constitution. The measurement method is hereinafter explained.

First, predetermined preparatory operations were made, in which, for example, a predetermined amount of the artificial urine 11 was placed into the vessel 2, and the air-inhaling pipe 3 was inserted into the vessel 2. Next, the filter paper 7 was mounted on the glass filter 6. On the other hand, in parallel with these mounting operations, 0.9 g of water-absorbent resin 12 was uniformly spread inside the supporting cylinder, namely, on the wire net 9, and the weight 10 was put on the water-absorbent resin 12.

Next, the wire net 9, namely, the supporting cylinder 8 (in which the water-absorbent resin 12 and the weight 10 were put), was mounted on the filter paper 7.

Then, weight $W_2$ (g) of the artificial urine 11, as absorbed by the water-absorbent resin 12 over a period of 60 minutes since the supporting cylinder 8 had been mounted on the filter paper 7, was measured with the scale 1.

Then, the absorption capacity (g/g) under a load, at 60 minutes after the initiation of the absorption, was calculated from weight $W_2$ in accordance with the following equation:

absorption capacity (g/g) under load=(weight $W_2$ (g))/(weight (g) of water-absorbent resin).

(c) Amount of Water-Soluble Component:

First, 0.500 g of water-absorbent resin was dispersed into 1,000 ml of deionized water and stirred for 16 hours, and then filtered with filter paper. Next, 50 g of the resultant filtrate was placed into a 100 ml beaker, and 1 ml of a 0.1 N aqueous sodium hydroxide solution, 10.00 ml of an N/200 aqueous methyl glycol chitosan solution, and 4 drops of a 0.1 wt % aqueous Toluidine Blue solution were added to the filtrate. Next, the resultant solution in the beaker was subjected to colloid titration with an N/400 aqueous potassium polyvinyl sulfate solution to determine titration amount Y (ml) assuming that the moment at which the color of the solution had changed from blue to red purple was the terminal of the titration. In addition, titration amount Z (ml) was determined by carrying out blank titration in the same way as the above-mentioned, except that 50 g of the filtrate was replaced with 50 g of deionized water. Then, the amount of the water-soluble component (wt %) was calculated from titration amounts Y and Z and from neutralization ratio W (mol %) of the acrylic acid, as provided for the production of the water-absorbent resin, in accordance with the following equation:

amount of water-soluble component (wt %)=(Z (ml)−Y (ml))× 0.01×[72·(100−W)+94W]/100.

(d) Absorption Speed:

First, 50 g of physiological salt solution (0.9 wt % aqueous NaCl solution), as adjusted to 30° C., and a stirring rod are placed into a beaker of 100 ml, and then stirred at a rate of 600 rpm with a magnetic stirrer. Then, if 2 g of water-absorbent resin is added into the beaker, gelation occurs to decrease the fluidity, and finally, the vortex of the stirring center disappears. A time, as spent from the addition of the sample till the disappearance of the vortex, was measured and regarded as the absorption speed.

(e) Urine Resistance Index (Stability of Swollen Gel to Urine):

First, 2 g of water-absorbent resin was swollen to 25 times with an artificial urine containing L-ascorbic acid of 0.005 wt % (composition of the artificial urine: 95 g of urea, 40 g of sodium chloride, 5 g of magnesium sulfate, 5 g of calcium chloride, 4,855 g of ion-exchanged water) in a plastic vessel of 100 ml with a cap, and then this vessel was capped and left to stand stationary under an atmosphere with a temperature of 37° C. and a relative humidity of 90% for 16 hours. Then, a distance, where the surface of the gel layer ran on a wall face of the vessel in 1 minute after tilting the vessel at 90°, was measured and regarded as the urine resistance index. The longer the running distance is, the worse the stability of the swollen gel to urine is.

(f) Liquid Permeation Speed of Absorbent Matter:

Hereinafter, first, a measurement apparatus as used for measuring the liquid permeation speed of the absorbent matter is simply explained while referring to FIGS. 2 and 3.

Figure 2:
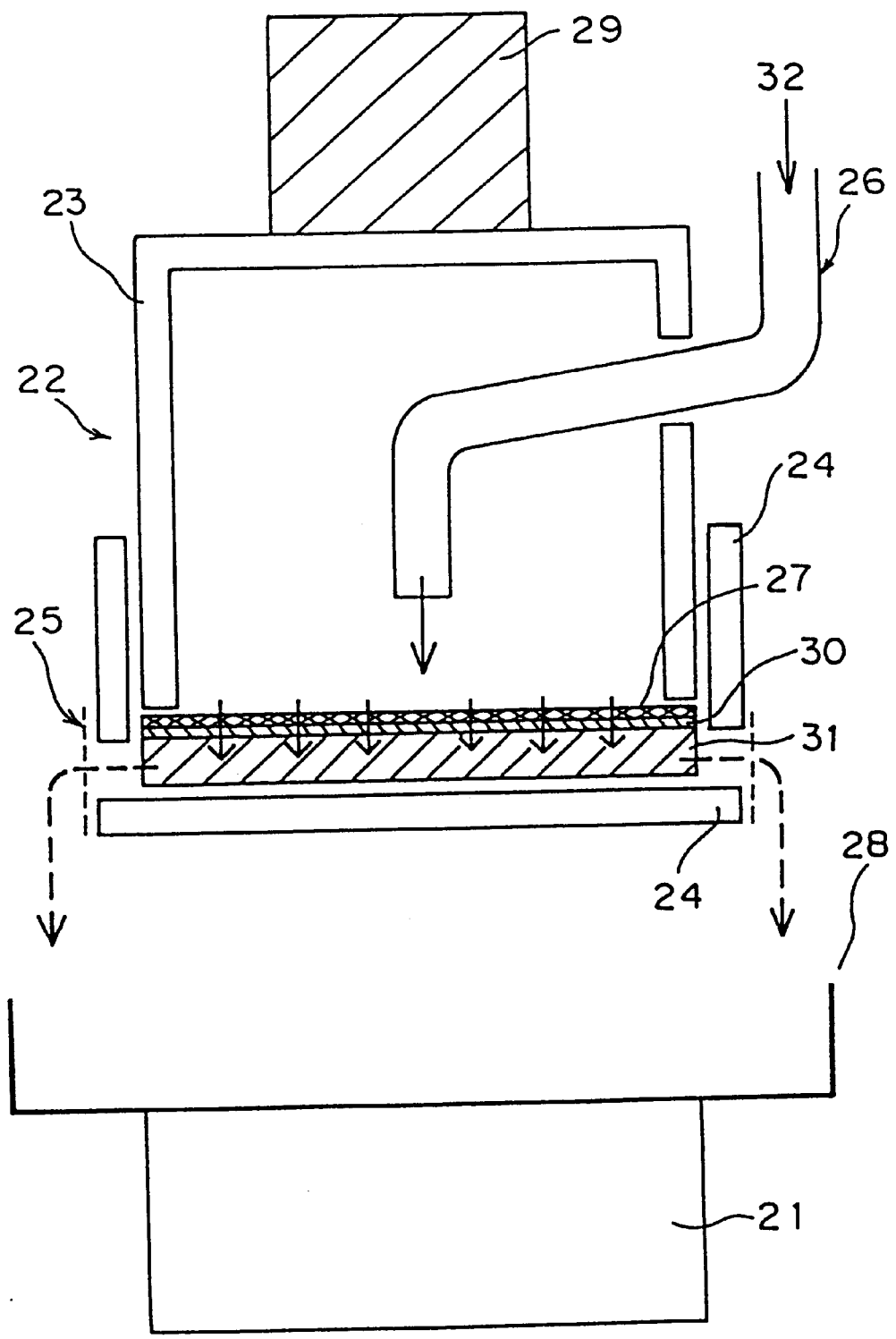
FIG. 2 is a schematic section of a measurement apparatus as used for measuring the liquid permeation speed of the absorbent matter.
Figure 3:
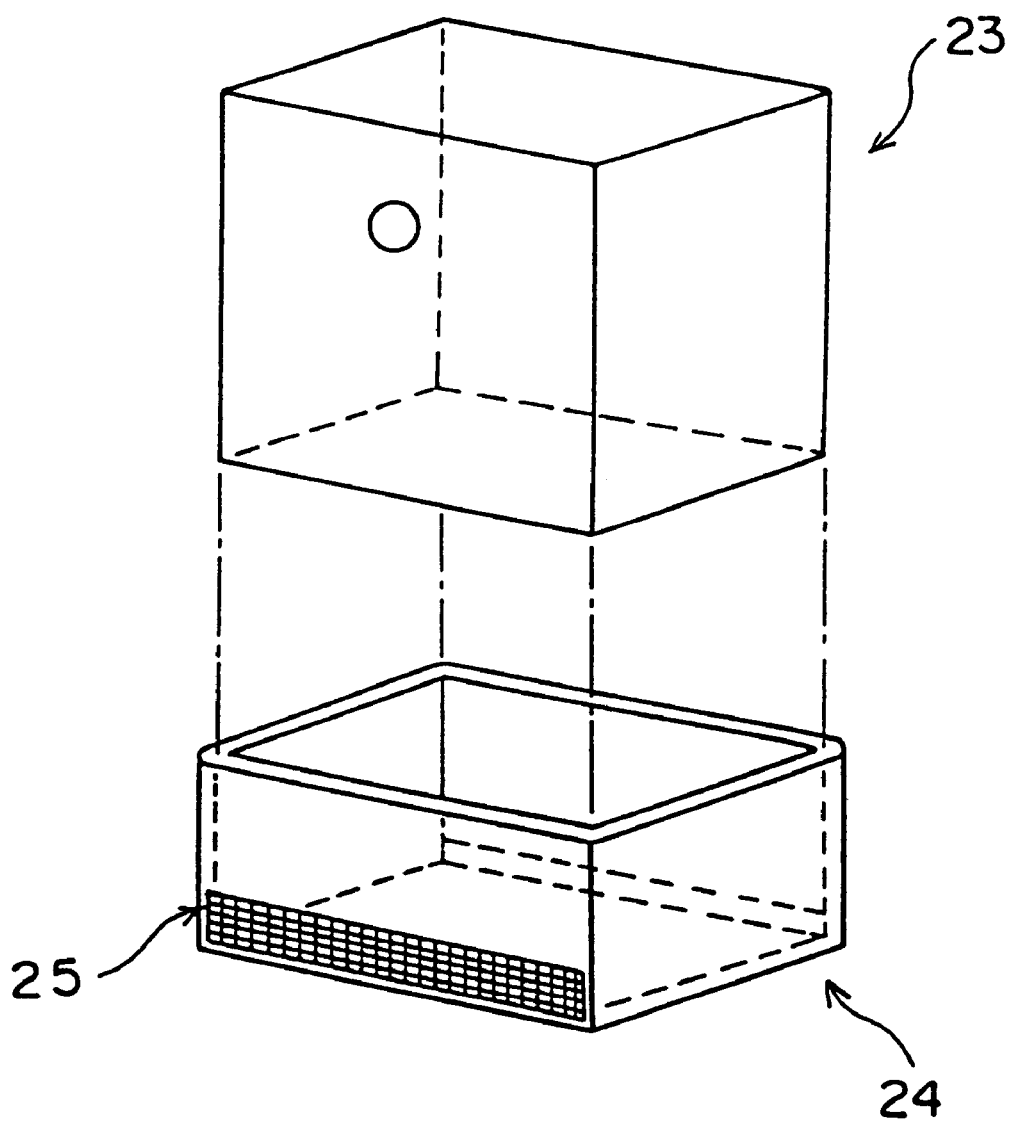
FIG. 3 is a perspective of a vessel as fitted to the measurement apparatus as used for measuring the liquid permeation speed of the absorbent matter.

As is shown in FIG. 2, the measurement apparatus comprises: a scale 21; a vessel 22, made of a transparent acryl plate, to contain an absorbent matter 31 as used for the measurement; an introducing tube 26; a wire net 27 (with a mesh size of 1 mm) on the absorbent matter 31; a vessel 28 on the scale 21; and a weight 29 as put on an upper part of the vessel 22 to contain the absorbent matter 31. As is shown in FIGS. 2 and 3, the vessel 22 to contain the absorbent matter 31 comprises the upper part 23 and a bottom part 24, and the bottom part 24 has an internal bottom face the shape of a 10 cm square. Each of opposite two of the four sides of the bottom part 24 has an opening with a depth of 5 mm and a width of 10 cm, and over each of these openings, a nylon net 25 (with a mesh size of 305 µm) is fixed for covering. Incidentally, in FIG. 3, only the nylon net on the front side is drawn, and the other nylon net on the back side is omitted from the drawing.

The weight 29 is regulated such that a load of 20 g/cm$^2$ can uniformly be applied to the wire net 27, namely, to the absorbent matter 31.

The liquid permeation speed of the absorbent matter was measured with the measurement apparatus having the above-mentioned constitution. The measurement method is hereinafter explained.

To measure the liquid permeation speed, the absorbent matter 31 as cut into a size of 10 cm×10 cm was first placed on the bottom part 24 of the vessel 22, and then a nonwoven fabric 30 (Heatlon G-S22 made by Nangoku Pulp Industry Co., Ltd.), as cut into a size of 10 cm×10 cm, the wire net 27, and the upper part 23 of the vessel 22 were mounted in sequence on the absorbent matter 31. Furthermore, the weight 29 was mounted on the upper part 23 of the vessel 22, thereby applying a load. Subsequently, the scale 21 and the vessel 28 thereon to receive a flowed-out liquid were put under the vessel 22.

Next, 50 ml of a physiological salt solution 32 (composition: 0.9 wt % aqueous NaCl solution) of 25° C., as prepared beforehand, was added through the introducing tube 26 at a flow rate of 7 ml/sec, and 20 minutes later, 50 ml of the liquid (physiological salt solution) was further added in the same way, when the amount of the liquid, as passed through the absorbent matter 31 and then flowed out from the nylon net 25 on the side parts of the vessel 22 and then collected into the vessel 28, was measured with the scale 21, thus determining the second-time liquid permeation speed. Furthermore, 20 minutes later than the second addition of the liquid, the third-time liquid permeation speed was measured in the same way. The liquid permeation speed (g/min) was the largest amount per unit time of the liquid as passed through in a period from the beginning till the end of the flowing-out of the liquid. As to an absorbent matter through which at most only 1 g of the liquid passed in 20 minutes, however, the largest amount per unit time of the liquid as passed through could not be determined, so the gram number of the amount of the liquid as flowed out in 20 minutes (g/20 min) was regarded as the liquid permeation speed (g/min).

REFERENTIAL EXAMPLE 1

A reaction solution was prepared by dissolving 4.96 g of polyethylene glycol diacrylate (average molar number of added ethylene oxide: 8) into 5,500 g of an aqueous solution of sodium acrylate with a neutralization ratio of 75 mol % (monomer concentration: 33 wt %). Next, this solution was degassed under a nitrogen gas atmosphere for 30 minutes, and then supplied into a reaction vessel as prepared by capping a stainless-steel-made double-arm type kneader of a capacity of 10 liters having two sigma type wings and a jacket. While maintaining the reaction solution at 30° C., the atmosphere inside the system was replaced with a nitrogen gas. Next, while the reaction solution was stirred, 2.46 g of sodium persulfate and 0.10 g of L-ascorbic acid were added, so that a polymerization reaction got started about 1 minute after. The polymerization was carried out at 30–80° C., and the resultant hydrogel polymer was separated out 60 minutes after the initiation of the polymerization.

The resultant hydrogel polymer had a finely divided diameter of about 5 mm. This finely divided hydrogel polymer was spread on a 50-mesh wire net and dried at 150° C. with hot air for 90 minutes. Then, the resultant dried product was pulverized with a vibration mill and further classified with a wire net of 20 mesh, thus obtaining a formless pulverized water-absorbent resin precursor (a).

A surface-crosslinking agent comprising 1 part by weight of propylene glycol, 0.05 parts by weight of ethylene glycol diglycidyl ether, 3 parts by weight of water, and 1 part by weight of isopropyl alcohol was mixed with 100 parts by weight of the resultant water-absorbent resin precursor (a). The resultant mixture was heated at 205° C. for 50 minutes, thus obtaining a water-absorbent resin (1), of which the average particle diameter was 360 μm, and of which the results of the absorption capacity under no load, the absorption capacity under a load, the amount of the water-soluble component, the absorption speed, and the urine resistance index are shown in Table 1.

REFERENTIAL EXAMPLE 2

A dried product of a hydrogel polymer, as obtained in the same way as of Referential Example 1, was pulverized with a vibration mill and further classified with a wire net of 20 mesh, thus obtaining a formless pulverized water-absorbent resin precursor (b). A surface-crosslinking agent comprising 0.05 parts by weight of glycerol, 0.05 parts by weight of ethylene glycol diglycidyl ether, 3 parts by weight of water, and 1 part by weight of isopropyl alcohol was mixed with 100 parts by weight of the resultant water-absorbent resin precursor (b). The resultant mixture was heated at 195° C. for 30 minutes, thus obtaining a water-absorbent resin (2), of which the average particle diameter was 450 μm, and of which the results of the absorption capacity under no load, the absorption capacity under a load, the amount of the water-soluble component, the absorption speed, and the urine resistance index are shown in Table 1.

REFERENTIAL EXAMPLE 3

A dried product of a hydrogel polymer, as obtained in the same way as of Referential Example 1, was pulverized with a vibration mill and further classified with a wire net of 20 mesh, thus obtaining a formless pulverized water-absorbent resin precursor (c). A surface-crosslinking agent comprising 1 part by weight of propylene glycol, 0.05 parts by weight of ethylene glycol diglycidyl ether, 3 parts by weight of water, and 1 part by weight of isopropyl alcohol was mixed with 100 parts by weight of the resultant water-absorbent resin precursor (c). The resultant mixture was heated at 210° C. for 45 minutes, thus obtaining a water-absorbent resin (3), of which the average particle diameter was 300 μm, and of which the results of the absorption capacity under no load, the absorption capacity under a load, the amount of the water-soluble component, the absorption speed, and the urine resistance index are shown in Table 1.

REFERENTIAL EXAMPLE 4

A reaction solution was prepared by dissolving 6.47 g of polyethylene glycol diacrylate (average molar number of added ethylene oxide: 8) into 5,500 g of an aqueous solution of sodium acrylate with a neutralization ratio of 65 mol % (monomer concentration: 30 wt %). Next, this solution was degassed under a nitrogen gas atmosphere for 30 minutes, and then supplied into a reaction vessel as prepared by capping a stainless-steel-made double-arm type kneader of a capacity of 10 liters having two sigma type wings and a jacket. While maintaining the reaction solution at 30° C., the atmosphere inside the system was replaced with a nitrogen gas. Next, while the reaction solution was stirred, 1.91 g of 2,2'-azobis(2-amidinopropane) dihydrochloride 0.96 g of sodium persulfate and 0.10 g of L-ascorbic acid were added, so that a polymerization reaction got started about 1 minute after. The polymerization was carried out at 30–80° C., and the resultant hydrogel polymer was separated out 60 minutes after the initiation of the polymerization.

The resultant hydrogel polymer had a finely divided diameter of about 5 mm. This finely divided hydrogel polymer was spread on a 50-mesh wire net and dried at 150° C. with hot air for 90 minutes. Then, the resultant dried product was pulverized with a vibration mill and further classified with a wire net of 20 mesh, thus obtaining a formless pulverized water-absorbent resin precursor (d).

A surface-crosslinking agent comprising 1 part by weight of propylene glycol, 0.025 parts by weight of ethylene glycol diglycidyl ether, 2 parts by weight of water, and 1 part by weight of isopropyl alcohol was mixed with 100 parts by weight of the resultant water-absorbent resin precursor (d). The resultant mixture was heated at 185° C. for 45 minutes, thus obtaining a water-absorbent resin (4), of which the average particle diameter was 450 μm, and of which the results of the absorption capacity under no load, the absorption capacity under a load, the amount of the water-soluble component, the absorption speed, and the urine resistance index are shown in Table 1.

REFERENTIAL EXAMPLE 5

A reaction solution was prepared by dissolving 3.49 g of trimethylolpropane triacrylate into 5,500 g of an aqueous solution of sodium acrylate with a neutralization ratio of 75 mol % (monomer concentration: 38 wt %). Next, this solution was degassed under a nitrogen gas atmosphere for 30 minutes, and then supplied into a reaction vessel as prepared by capping a stainless-steel-made double-arm type kneader of a capacity of 10 liters having two sigma type wings and a jacket. While maintaining the reaction solution at 30° C., the atmosphere inside the system was replaced with a nitrogen gas. Next, while the reaction solution was stirred, 2.83 g of sodium persulfate and 0.12 g of L-ascorbic acid were added, so that a polymerization reaction got started about 1 minute after. The polymerization was carried out at 30–80° C., and the resultant hydrogel polymer was separated out 60 minutes after the initiation of the polymerization.

The resultant hydrogel polymer had a finely divided diameter of about 5 mm. This finely divided hydrogel polymer was spread on a 50-mesh wire net and dried at 150° C. with hot air for 90 minutes. Then, the resultant dried product was pulverized with a vibration mill and further classified with a wire net of 20 mesh, thus obtaining a formless pulverized water-absorbent resin precursor (e).

A surface-crosslinking agent comprising 0.5 parts by weight of glycerol, 2 parts by weight of water, and 0.5 parts by weight of isopropyl alcohol was mixed with 100 parts by weight of the resultant water-absorbent resin precursor (e). The resultant mixture was heated at 210° C. for 50 minutes, thus obtaining a water-absorbent resin (5), of which the average particle diameter was 380 μm, and of which the results of the absorption capacity under no load, the absorption capacity under a load, the amount of the water-soluble component, the absorption speed, and the urine resistance index are shown in Table 1.

REFERENTIAL EXAMPLE 6

A reaction solution was prepared by dissolving 5.95 g of polyethylene glycol diacrylate (average molar number of added ethylene oxide: 8) into 5,500 g of an aqueous solution of sodium acrylate with a neutralization ratio of 75 mol % (monomer concentration: 33 wt %). Next, this solution was degassed under a nitrogen gas atmosphere for 30 minutes, and then supplied into a reaction vessel as prepared by capping a stainless-steel-made double-arm type kneader of a capacity of 10 liters having two sigma type wings and a jacket. While maintaining the reaction solution at 30° C., the atmosphere inside the system was replaced with a nitrogen gas. Next, while the reaction solution was stirred, 2.46 g of sodium persulfate and 0.10 g of L-ascorbic acid were added, so that a polymerization reaction got started about 1 minute after. The polymerization was carried out at 30–80° C., and the resultant hydrogel polymer was separated out 60 minutes after the initiation of the polymerization.

The resultant hydrogel polymer had a finely divided diameter of about 5 mm. This finely divided hydrogel polymer was spread on a 50-mesh wire net and dried at 150° C. with hot air for 90 minutes. Then, the resultant dried product was pulverized with a vibration mill and further classified with a wire net of 20 mesh, thus obtaining a formless pulverized water-absorbent resin precursor (f).

A surface-crosslinking agent comprising 0.05 parts by weight of 1,3-propanediol, 4 parts by weight of water, and 4 parts by weight of isopropyl alcohol was mixed with 100 parts by weight of the resultant water-absorbent resin precursor (f). The resultant mixture was heated at 195° C. for 60 minutes, thus obtaining a water-absorbent resin (6), of which the average particle diameter was 450 μm, and of which the results of the absorption capacity under no load, the absorption capacity under a load, the amount of the water-soluble component, the absorption speed, and the urine resistance index are shown in Table 1.

REFERENTIAL EXAMPLE 7

A reaction solution was prepared by dissolving 2.10 g of trimethylolpropane triacrylate into 5,500 g of an aqueous solution of sodium acrylate with a neutralization ratio of 75 mol % (monomer concentration: 38 wt %). Next, this solution was degassed under a nitrogen gas atmosphere for 30 minutes, and then supplied into a reaction vessel as prepared by capping a stainless-steel-made double-arm type kneader of a capacity of 10 liters having two sigma type wings and a jacket. While maintaining the reaction solution at 30° C., the atmosphere inside the system was replaced with a nitrogen gas. Next, while the reaction solution was stirred, 2.83 g of sodium persulfate and 0.12 g of L-ascorbic acid were added, so that a polymerization reaction got started about 1 minute after. The polymerization was carried out at 30–80° C., and the resultant hydrogel polymer was separated out 60 minutes after the initiation of the polymerization.

The resultant hydrogel polymer had a finely divided diameter of about 5 mm. This finely divided hydrogel polymer was spread on a 50-mesh wire net and dried at 150° C. with hot air for 90 minutes. Then, the resultant dried product was pulverized with a vibration mill and further classified with a wire net of 20 mesh, thus obtaining a formless pulverized water-absorbent resin precursor (g).

A surface-crosslinking agent comprising 0.5 parts by weight of glycerol, 2 parts by weight of water, and 0.5 parts by weight of isopropyl alcohol was mixed with 100 parts by weight of the resultant water-absorbent resin precursor (g). The resultant mixture was heated at 210° C. for 50 minutes, thus obtaining a water-absorbent resin (7), of which the average particle diameter was 360 μm, and of which the results of the absorption capacity under no load, the absorption capacity under a load, the amount of the water-soluble component, the absorption speed, and the urine resistance index are shown in Table 1.

REFERENTIAL EXAMPLE 8

A reaction solution was prepared by dissolving 6.99 g of trimethylolpropane triacrylate into 5,500 g of an aqueous solution of sodium acrylate with a neutralization ratio of 75 mol % (monomer concentration: 38 wt %). Next, this solution was degassed under a nitrogen gas atmosphere for 30 minutes, and then supplied into a reaction vessel as prepared by capping a stainless-steel-made double-arm type kneader of a capacity of 10 liters having two sigma type wings and a jacket. While maintaining the reaction solution at 30° C., the atmosphere inside the system was replaced with a nitrogen gas. Next, while the reaction solution was stirred, 2.83 g of sodium persulfate and 0.12 g of L-ascorbic acid were added, so that a polymerization reaction got started about 1 minute after. The polymerization was carried out at 30–80° C., and the resultant hydrogel polymer was separated out 60 minutes after the initiation of the polymerization.

The resultant hydrogel polymer had a finely divided diameter of about 5 mm. This finely divided hydrogel polymer was spread on a 50-mesh wire net and dried at 150° C. with hot air for 90 minutes. Then, the resultant dried product was pulverized with a vibration mill and further classified with a wire net of 20 mesh, thus obtaining a formless pulverized water-absorbent resin (8), of which the average particle diameter was 380 μm, and of which the results of the absorption capacity under no load, the absorption capacity under a load, the amount of the water-soluble component, the absorption speed, and the urine resistance index are shown in Table 1.

REFERENTIAL EXAMPLE 9

First, 800 g of cyclohexane was placed into a 4-necked separable flask of 2,000 ml as equipped with a stirrer, a reflux condenser, a thermometer, a nitrogen gas-introducing tube, and a dropping funnel. Then, 3.0 g of sorbitan monostearate was added and dissolved as a dispersant, and a nitrogen gas was blown into the resultant mixture to eliminate oxygen as dissolved therein.

On the other hand, an aqueous monomer solution comprising 141 g of sodium acrylate, 36 g of acrylic acid, 0.154 g of methylenebisacrylamide, and 413 g of ion-exchanged water was prepared in another flask, and a nitrogen gas was blown into the resultant aqueous monomer solution to eliminate oxygen as dissolved therein.

Next, 1.0 g of a 10 wt % aqueous sodium persulfate solution was added to the aqueous monomer solution in the flask, and the entirety of the resultant mixture was added into the foregoing separable flask and dispersed by stirring at 230 rpm. Then, the bath temperature was raised to 60° C. to initiate a polymerization reaction and kept at the same temperature for 2 hours to complete the polymerization.

After the completion of the polymerization, most of water was distilled off by azeotropic dehydration, thus obtaining a cyclohexane suspension of the resultant polymer. This suspension was filtered, thus obtaining a resin with a water content of 20 wt %, and further, this resin was dried under vacuum at 80° C., thus obtaining a water-absorbent resin precursor (h) with a water content of 5 wt %.

Next, 10 g of the resultant water-absorbent resin precursor (h) was added to 500 ml of methanol as heated to 60° C., and the resultant mixture was stirred for 1 hour, and then filtered and dried.

A surface-crosslinking agent comprising 1.0 part by weight of propylene glycol, 0.05 parts by weight of ethylene glycol diglycidyl ether, 3 parts by weight of water, and 1 part by weight of isopropyl alcohol was mixed with 100 parts by weight of the above-treated water-absorbent resin precursor. The resultant mixture was heated at 185° C. for 50 minutes, thus obtaining a water-absorbent resin (9), of which the average particle diameter was 128 μm, and of which the results of the absorption capacity under no load, the absorption capacity under a load, the amount of the water-soluble component, the absorption speed, and the urine resistance index are shown in Table 1.

REFERENTIAL EXAMPLE 10

An amount of 0.3 parts by weight of hydrophilic fine particle-shaped silicon dioxide (trade name: Aerosil 200, made by Nippon Aerosil Co., Ltd.) was added to 100 parts by weight of the water-absorbent resin (1) as obtained in Referential Example 1, thus obtaining a water-absorbent resin (10), of which the average particle diameter was 360 μm, and of which the results of the absorption capacity under no load, the absorption capacity under a load, the amount of the water-soluble component, the absorption speed, and the urine resistance index are shown in Table 1.

REFERENTIAL EXAMPLE 11

An amount of 0.3 parts by weight of hydrophilic fine particle-shaped silicon dioxide (trade name: CARPLEX® 22S, made by SHIONOGI & CO., LTD.) was added to 100 parts by weight of the water-absorbent resin (5) as obtained in Referential Example 5, thus obtaining a water-absorbent resin (11), of which the average particle diameter was 380 μm, and of which the results of the absorption capacity under no load, the absorption capacity under a load, the amount of the water-soluble component, the absorption speed, and the urine resistance index are shown in Table 1.

TABLE 1

|  | Absorption capacity under no load (g/g) | Absorption capacity under load (g/g) | Amount of water-soluble component (wt %) | Absorption speed (second) | Urine resistance index (mm) |
|---|---|---|---|---|---|
| Water-absorbent resin (1) | 44 | 37 | 14 | 50 | 0 |
| Water-absorbent resin (2) | 47 | 32 | 14 | 89 | 0 |
| Water-absorbent resin (3) | 42 | 34 | 14 | 42 | 0 |
| Water-absorbent resin (4) | 60 | 13 | 13 | 48 | 0 |
| Water-absorbent resin (5) | 38 | 28 | 10 | 76 | 0 |
| Water-absorbent resin (6) | 47 | 10 | 13 | 85 | 0 |
| Water-absorbent resin (7) | 41 | 11 | 16 | 40 | 10 |
| Water-absorbent resin (8) | 40 | 8 | 7 | 105 | 0 |
| Water-absorbent resin (9) | 40 | 41 | 22 | 20 | 1 |
| Water-absorbent resin (10) | 43 | 33 | 14 | 46 | 0 |
| Water-absorbent resin (11) | 38 | 27 | 10 | 68 | 0 |

EXAMPLE 1

First, 50 parts by weight of the water-absorbent resin (1), as obtained in Referential Example 1, and 50 parts by weight of wood-pulverized pulp were mixed together in a dry manner with a mixer. Next, the resultant mixture was shaped into a web of the size of 120 mm×380 mm by pneumatically molding the mixture on a wire screen of 400 mesh (mesh size: 38 μm) with a batch type pneumatic device. In addition, this web was pressed for 5 seconds under a pressure of 2 kg/cm², thus obtaining an absorbent matter (1) of a weight of about 526 g/m².

Next, a back sheet (liquid-impermeable sheet) of a liquid-impermeable polypropylene with a so-called leg gather, the above-mentioned absorbent matter (1), and a top sheet (liquid-permeable sheet) of a liquid-permeable polypropylene were attached to each other in this order with double coated tapes, and two so-called tape fasteners were then provided to the resultant attached product, thus obtaining an absorbent article (1) (i.e. disposable diaper). The weight of this absorbent article was 47 g.

This absorbent article was fitted up to each of four units of so-called kewpie dolls (three units of which had a body length of 55 cm and a weight of 5 kg, and the other one unit had a body length of 65 cm and a weight of 6 kg), and these dolls were laid on their faces. Then, a tube was inserted between the absorbent article and the dolls, and 50 ml of a physiological salt solution was injected through the tube every 20 minutes to a position corresponding to where urine is discharged on the human body. This injection operation was ended when the injected physiological salt solution began leaking without being absorbed by the absorbent article, and the amount of the physiological salt solution, as had been injected until then, was measured, and the average value thereof for the above-mentioned four units of kewpie dolls was regarded as the absorption amount of the absorbent article in a state of lying face down. The result thereof is shown in Table 2 along with a value of the concentration absorption index. In addition, Table 2 further shows results of the measurement of the second-time and the third-time liquid permeation speed under a load for the above-mentioned absorbent matter (1) as cut into a size of 10 cm×10 cm. Incidentally, the measurement of the second-time liquid permeation speed ($\gamma$) of a pulp mat resulted in 80 (g/min), wherein the pulp mat was prepared by shaping 5.5 g of the above-mentioned wood-pulverized pulp into a web of the size of 10 cm×10 cm and then pressing the resultant web for 5 seconds under a pressure of 2 kg/cm$^2$.

EXAMPLE 2

An absorbent matter (2) and an absorbent article (2) were obtained in the same way as of Example 1 except that the water-absorbent resin (1), as obtained in Referential Example 1, was replaced with the water-absorbent resin (2) as obtained in Referential Example 2. The resultant absorbent article weighed 47 g.

The absorption amount of this absorbent article in a state of lying face down was determined in the same way as of Example 1. The result thereof is shown in Table 2 along with a value of the concentration absorption index.

EXAMPLE 3

An absorbent matter (3) and an absorbent article (3) were obtained in the same way as of Example 1 except that the water-absorbent resin (1), as obtained in Referential Example 1, was replaced with the water-absorbent resin (3) as obtained in Referential Example 3. The resultant absorbent article weighed 47 g.

The absorption amount of this absorbent article in a state of lying face down was determined in the same way as of Example 1. The result thereof is shown in Table 2 along with a value of the concentration absorption index. In addition, Table 2 further shows results of the measurement of the second-time and the third-time liquid permeation speed under a load for the above-mentioned absorbent matter (3) as cut into a size of 10 cm×10 cm.

EXAMPLE 4

An absorbent matter (4) and an absorbent article (4) were obtained in the same way as of Example 1 except that the water-absorbent resin (1), as obtained in Referential Example 1, was replaced with the water-absorbent resin (4) as obtained in Referential Example 4. The resultant absorbent article weighed 47 g.

The absorption amount of this absorbent article in a state of lying face down was determined in the same way as of Example 1. The result thereof is shown in Table 2 along with a value of the concentration absorption index.

EXAMPLE 5

An absorbent matter (5) and an absorbent article (5) were obtained in the same way as of Example 1 except that the water-absorbent resin (1), as obtained in Referential Example 1, was replaced with the water-absorbent resin (5) as obtained in Referential Example 5. The resultant absorbent article weighed 47 g.

The absorption amount of this absorbent article in a state of lying face down was determined in the same way as of Example 1. The result thereof is shown in Table 2 along with a value of the concentration absorption index. In addition, Table 2 further shows results of the measurement of the second-time and the third-time liquid permeation speed under a load for the above-mentioned absorbent matter (5) as cut into a size of 10 cm×10 cm.

EXAMPLE 6

An absorbent matter (6) and an absorbent article (6) were obtained in the same way as of Example 1 except that the water-absorbent resin (1), as obtained in Referential Example 1, was replaced with the water-absorbent resin (6) as obtained in Referential Example 6. The resultant absorbent article weighed 47 g.

The absorption amount of this absorbent article in a state of lying face down was determined in the same way as of Example 1. The result thereof is shown in Table 2 along with a value of the concentration absorption index.

EXAMPLE 7

An absorbent matter (7) and an absorbent article (7) were obtained in the same way as of Example 1 except that the water-absorbent resin (1), as obtained in Referential Example 1, was replaced with the water-absorbent resin (7) as obtained in Referential Example 7. The resultant absorbent article weighed 47 g.

The absorption amount of this absorbent article in a state of lying face down was determined in the same way as of Example 1. The result thereof is shown in Table 2 along with a value of the concentration absorption index.

EXAMPLE 8

An absorbent matter (8) and an absorbent article (8) were obtained in the same way as of Example 1 except that the water-absorbent resin (1), as obtained in Referential Example 1, was replaced with the water-absorbent resin (8) as obtained in Referential Example 8. The resultant absorbent article weighed 47 g.

The absorption amount of this absorbent article in a state of lying face down was determined in the same way as of Example 1. The result thereof is shown in Table 2 along with a value of the concentration absorption index.

EXAMPLE 9

An absorbent matter (9) and an absorbent article (9) were obtained in the same way as of Example 1 except that the water-absorbent resin (1), as obtained in Referential Example 1, was replaced with the water-absorbent resin (9) as obtained in Referential Example 9. The resultant absorbent article weighed 47 g.

The absorption amount of this absorbent article in a state of lying face down was determined in the same way as of Example 1. The result thereof is shown in Table 2 along with a value of the concentration absorption index. In addition, Table 2 further shows results of the measurement of the second-time and the third-time liquid permeation speed under a load for the above-mentioned absorbent matter (9) as cut into a size of 10 cm×10 cm.

EXAMPLE 10

An absorbent matter (10) and an absorbent article (10) were obtained in the same way as of Example 1 except that the water-absorbent resin (1), as obtained in Referential Example 1, was replaced with the water-absorbent resin (10) as obtained in Referential Example 10. The resultant absorbent article weighed 47 g.

The absorption amount of this absorbent article in a state of lying face down was determined in the same way as of Example 1. The result thereof is shown in Table 2 along with a value of the concentration absorption index. In addition, Table 2 further shows results of the measurement of the second-time and the third-time liquid permeation speed under a load for the above-mentioned absorbent matter (10) as cut into a size of 10 cm×10 cm.

TABLE 2

| | Water-absorbent resin used | Concentration absorption index | Liquid permeability of absorbent matter (g/min) | | Absorption amount in state of lying face down (g) |
|---|---|---|---|---|---|
| | | | second time | third time | |
| Example (1) | Water-absorbent resin (1) | 40.5 | 15.1 | 17.9 | 288 |
| Example (2) | Water-absorbent resin (2) | 39.5 | — | — | 263 |
| Example (3) | Water-absorbent resin (3) | 38.0 | 31.8 | 21.0 | 263 |
| Example (4) | Water-absorbent resin (4) | 36.5 | — | — | 250 |
| Example (5) | Water-absorbent resin (5) | 33.0 | 34.1 | 41.2 | 238 |
| Example (6) | Water-absorbent resin (6) | 28.5 | — | — | 238 |
| Example (7) | Water-absorbent resin (7) | 26.0 | — | — | 200 |
| Example (8) | Water-absorbent resin (8) | 24.0 | — | — | 225 |
| Example (9) | Water-absorbent resin (9) | 40.5 | 11.5 | 7.0 | 275 |
| Example (10) | Water-absorbent resin (10) | 38.0 | 23.6 | 26.5 | 263 |

$\gamma(1-\alpha) = 40$ (g/min)

From Tables 1 and 2 above, it would be understood that the higher the concentration absorption index is, the larger the absorption amount in a state of lying face down is, and that even if the absorption capacity under no load and the absorption capacity under a load are different between the water-absorbent resins (1) to (11), the absorption amount in a state near to practical use of the absorbent article can be predicted by introducing the concentration absorption index as defined in the present invention. Incidentally, it was shown that the absorbent matters of which the liquid permeation speeds were measured were all within the preferable range.

EXAMPLE 11

First, 75 parts by weight of the water-absorbent resin (1), as obtained in Referential Example 1, and 25 parts by weight of wood-pulverized pulp were mixed together in a dry manner with a mixer. Next, the resultant mixture was shaped into a web of the size of 120 mm×350 mm by pneumatically molding the mixture on a wire screen of 400 mesh (mesh size: 38 μm) with a batch type pneumatic device. In addition, this web was pressed for 5 seconds under a pressure of 2 kg/cm², thus obtaining an absorbent matter (11) of a weight of about 500 g/m².

Next, a back sheet (liquid-impermeable sheet) of a liquid-impermeable polypropylene with a so-called leg gather, the above-mentioned absorbent matter, and a top sheet (liquid-permeable sheet) of a liquid-permeable polypropylene were attached to each other in this order with double coated tapes, and two so-called tape fasteners were then provided to the resultant attached product, thus obtaining an absorbent article (11) (i.e. disposable diaper). The weight of this absorbent article was 44 g.

This absorbent article was fitted up to each of four units of so-called kewpie dolls (three units of which had a body length of 55 cm and a weight of 5 kg, and the other one unit had a body length of 65 cm and a weight of 6 kg), and these dolls were laid on their faces. Then, a tube was inserted between the absorbent article and the dolls, and 50 ml of a physiological salt solution was injected through the tube every 20 minutes to a position corresponding to where urine is discharged on the human body. This injection operation was ended when the injected physiological salt solution began leaking without being absorbed by the absorbent article, and the amount of the physiological salt solution, as had been injected until then, was measured, and the average value thereof for the above-mentioned four units of kewpie dolls was regarded as the absorption amount of the absorbent article in a state of lying face down. The result thereof is shown in Table 3 along with a value of the concentration absorption index.

In addition, Table 3 further shows results of the measurement of the second-time and the third-time liquid permeation speed under a load for the above-mentioned absorbent matter (11) as cut into a size of 10 cm×10 cm. Incidentally, the measurement of the second-time liquid permeation speed ($\gamma$) of a pulp mat resulted in 80 (g/min), wherein the pulp mat was prepared by shaping 5.5 g of the above-mentioned wood-pulverized pulp into a web of the size of 10 cm×10 cm and then pressing the resultant web for 5 seconds under a pressure of 2 kg/cm².

EXAMPLE 12

An absorbent matter (12) and an absorbent article (12) were obtained in the same way as of Example 11 except that the water-absorbent resin (1), as obtained in Referential Example 1, was replaced with the water-absorbent resin (2) as obtained in Referential Example 2. The resultant absorbent article weighed 44 g.

The absorption amount of this absorbent article in a state of lying face down was determined in the same way as of Example 11. The result thereof is shown in Table 3 along with a value of the concentration absorption index.

EXAMPLE 13

An absorbent matter (13) and an absorbent article (13) were obtained in the same way as of Example 11 except that the water-absorbent resin (1), as obtained in Referential Example 1, was replaced with the water-absorbent resin (3) as obtained in Referential Example 3. The resultant absorbent article weighed 44 g.

The absorption amount of this absorbent article in a state of lying face down was determined in the same way as of Example 11. The result thereof is shown in Table 3 along with a value of the concentration absorption index. In addition, Table 3 further shows results of the measurement of the second-time and the third-time liquid permeation speed under a load for the above-mentioned absorbent matter (13) as cut into a size of 10 cm×10 cm.

EXAMPLE 14

An absorbent matter (14) and an absorbent article (14) were obtained in the same way as of Example 11 except that the water-absorbent resin (1), as obtained in Referential Example 1, was replaced with the water-absorbent resin (4) as obtained in Referential Example 4. The resultant absorbent article weighed 44 g.

The absorption amount of this absorbent article in a state of lying face down was determined in the same way as of Example 11. The result thereof is shown in Table 3 along with a value of the concentration absorption index.

EXAMPLE 15

An absorbent matter (15) and an absorbent article (15) were obtained in the same way as of Example 11 except that the water-absorbent resin (1), as obtained in Referential Example 1, was replaced with the water-absorbent resin (5) as obtained in Referential Example 5. The resultant absorbent article weighed 44 g.

The absorption amount of this absorbent article in a state of lying face down was determined in the same way as of Example 11. The result thereof is shown in Table 3 along with a value of the concentration absorption index. In addition, Table 3 further shows results of the measurement of the second-time and the third-time liquid permeation speed under a load for the above-mentioned absorbent matter (15) as cut into a size of 10 cm×10 cm.

EXAMPLE 16

An absorbent matter (16) and an absorbent article (16) were obtained in the same way as of Example 11 except that the water-absorbent resin (1), as obtained in Referential Example 1, was replaced with the water-absorbent resin (6) as obtained in Referential Example 6. The resultant absorbent article weighed 44 g.

The absorption amount of this absorbent article in a state of lying face down was determined in the same way as of Example 11. The result thereof is shown in Table 3 along with a value of the concentration absorption index.

EXAMPLE 17

An absorbent matter (17) and an absorbent article (17) were obtained in the same way as of Example 11 except that the water-absorbent resin (1), as obtained in Referential Example 1, was replaced with the water-absorbent resin (7) as obtained in Referential Example 7. The resultant absorbent article weighed 44 g.

The absorption amount of this absorbent article in a state of lying face down was determined in the same way as of Example 11. The result thereof is shown in Table 3 along with a value of the concentration absorption index.

EXAMPLE 18

An absorbent matter (18) and an absorbent article (18) were obtained in the same way as of Example 11 except that the water-absorbent resin (1), as obtained in Referential Example 1, was replaced with the water-absorbent resin (8) as obtained in Referential Example 8. The resultant absorbent article weighed 44 g.

The absorption amount of this absorbent article in a state of lying face down was determined in the same way as of Example 11. The result thereof is shown in Table 3 along with a value of the concentration absorption index.

EXAMPLE 19

An absorbent matter (19) and an absorbent article (19) were obtained in the same way as of Example 11 except that the water-absorbent resin (1), as obtained in Referential Example 1, was replaced with the water-absorbent resin (9) as obtained in Referential Example 9. The resultant absorbent article weighed 44 g.

The absorption amount of this absorbent article in a state of lying face down was determined in the same way as of Example 11. The result thereof is shown in Table 3 along with a value of the concentration absorption index. In addition, Table 3 further shows results of the measurement of the second-time and the third-time liquid permeation speed under a load for the above-mentioned absorbent matter (19) as cut into a size of 10 cm×10 cm.

EXAMPLE 20

An absorbent matter (20) and an absorbent article (20) were obtained in the same way as of Example 11 except that the water-absorbent resin (1), as obtained in Referential Example 1, was replaced with the water-absorbent resin (10) as obtained in Referential Example 10. The resultant absorbent article weighed 44 g.

The absorption amount of this absorbent article in a state of lying face down was determined in the same way as of Example 11. The result thereof is shown in Table 3 along with a value of the concentration absorption index. In addition, Table 3 further shows results of the measurement of the second-time and the third-time liquid permeation speed under a load for the above-mentioned absorbent matter (20) as cut into a size of 10 cm×10cm.

EXAMPLE 21

An absorbent matter (21) and an absorbent article (21) were obtained in the same way as of Example 11 except that the water-absorbent resin (1), as obtained in Referential Example 1, was replaced with the water-absorbent resin (11) as obtained in Referential Example 11. The resultant absorbent article weighed 44 g.

The absorption amount of this absorbent article in a state of lying face down was determined in the same way as of Example 11. The result thereof is shown in Table 3 along with a value of the concentration absorption index. In addition, Table 3 further shows results of the measurement of the second-time and the third-time liquid permeation speed under a load for the above-mentioned absorbent matter (21) as cut into a size of 10 cm×10 cm.

TABLE 3

| | Water-absorbent resin used | Concentration absorption index | Liquid permeability of absorbent matter (g/min) | | Absorption amount in state of lying face down (g) |
|---|---|---|---|---|---|
| | | | second time | third time | |
| Example (11) | Water-absorbent resin (1) | 38.8 | 2.9 | 0.78 | 288 |
| Example (12) | Water-absorbent resin (2) | 35.8 | — | — | 275 |
| Example (13) | Water-absorbent resin (3) | 36.0 | 1.0 | 0.37 | 288 |
| Example (14) | Water-absorbent resin (4) | 24.8 | — | — | 250 |
| Example (15) | Water-absorbent resin(5) | 30.5 | 5.1 | 3.56 | 263 |
| Example (16) | Water-absorbent resin (6) | 19.3 | — | — | 250 |
| Example (17) | Water-absorbent resin (7) | 18.5 | — | — | 225 |
| Example (18) | Water-absorbent resin (8) | 16.0 | — | — | 225 |
| Example (19) | Water-absorbent resin (9) | 40.8 | 0.0* | 0.03 | 275 |
| Example (20) | Water-absorbent resin (10) | 35.5 | 26.0 | 2.64 | 263 |
| Example (21) | Water-absorbent resin (11) | 29.8 | 28.0 | 3.43 | 238 |

*Because the absorbent matter entirely absorbed the liquid, the liquid did not flow out. $\gamma(1-\alpha) = 20$ (g/min)

From Table 3 above, it would be understood that the water-absorbent resin with a concentration absorption index of 35 or more displays a large absorption amount in a state of lying face down and a large absorption amount in a state near to practical use of the absorbent article. As to the absorbent article (9), however, because the third-time liquid permeation speed of the absorbent matter is slow, the absorption amount in a state of lying face down is smaller than that as expected from the concentration absorption index. Similarly, as to the absorbent article (10), because the second-time liquid permeation speed of the absorbent matter is fast, the absorption amount in a state of lying face down is smaller than that as expected from the concentration absorption index.

EXAMPLE 22

As to five commercially available diapers as shown in Table 4, the following properties were measured: the ratio by weight of the water-absorbent resin to the total of the water-absorbent resin and the fibrous material (water-absorbent resin concentration), the absorption capacities of the water-absorbent resin under no load and under a load, the liquid permeation speed ($\gamma$) of the fibrous material, the liquid permeation speed of the absorbent matter in the diaper, and the absorption amount of the diaper in a state of lying face down. Results are shown in Table 4.

The respective measurement methods of the properties are as follows:

(1) Water-Absorbent Resin Concentration:

Each commercially available diaper was dried under vacuum at 60° C. for 16 hours. Components such as the back sheet, the top sheet, and the nonwoven fabric sheet were removed from the diaper, and the weight X (g) of the resultant absorbent layer mainly comprising the water-absorbent resin and the fibrous material was measured. The weight Y (g) of the water-absorbent resin in the absorbent layer was also determined to calculate the water-absorbent resin concentration in accordance with the following equation:

$$\text{water-absorbent resin concentration} = Y/X.$$

(2) Absorption Capacities of Water-Absorbent Resin Under No Load and Under Load:

The water-absorbent resin and the pulp were separated from the absorbent matter of each commercially available diaper and then dried under vacuum at 60° C. for 16 hours. Then, the absorption capacities of the resultant water-absorbent resin under no load and under a load were measured.

(3) Liquid Permeation Speed ($\gamma$) of Fibrous Material:

The water-absorbent resin and the fibrous material were separated from the absorbent matter of each commercially available diaper and then dried under vacuum at 60° C. for 16 hours. Then, 5.5 g of the resultant fibrous material was shaped into a web of the size of 10 cm×10 cm and then pressed for 5 seconds under a pressure of 2 kg/cm$^2$, thus preparing a mat of the fibrous material. The second-time liquid permeation speed of the resultant mat was measured to determine the value of $\gamma$ (g/min).

(4) Liquid Permeation Speed of Absorbent Matter in Diaper:

A portion, corresponding to a portion to receive urine as discharged from a human body during practical use, of each commercially available diaper was cut into the size of 10 cm×10 cm, and the portions thereof (such as the back sheet and the top sheet) other than the layer mainly comprising the water-absorbent resin and the fibrous material were all removed, thus obtaining an absorbent matter (mainly comprising the water-absorbent resin and the fibrous material) of the size of 10 cm×10 cm. The second-time and the third-time liquid permeation speed of this absorbent matter were measured.

(5) Absorption Amount of Diaper in State of Lying Face Down:

The absorption amount of the absorbent article (diaper) in a state of lying face down was measured in the same way as of Example 1 using the same kewpie dolls as those used in Example 1.

TABLE 4

| Trade name | Size | Maker | Production country | Water-absorbent resin concentration | Absorption capacity under no load (g/g) | Absorption capacity under load (g/g) | Concentration absorption index | Liquid permeation speed γ of fibrous material (g/min) | Liquid permeability of absorbent matter (g/min) second time | Liquid permeability of absorbent matter (g/min) third time | Absorption amount in state of lying face down (g) |
|---|---|---|---|---|---|---|---|---|---|---|---|
| Moony Power Slim | L | UNI-CHARM K.K. | Japan | 0.50 | 45 | 12 | 28.5 | 76 | 29.4 | 21.9 | 188 |
| Pampers Sara-Sara Care | L | Procter & Gamble Far East, Inc. | Japan | 0.47 | 39 | 27 | 33.4 | 75 | 15.2 | 19.3 | 238 |
| Pampers BABY-DRY STRETCH | 4 | Procter & Gamble | USA | 0.47 | 38 | 8 | 23.9 | 68 | 9.0 | 24.0 | 200 |
| HUGGIES Ultratrim | 4 | Kimbery-Clark Corporation | USA | 0.41 | 40 | 18 | 31.0 | 95 | 12.0 | 24.0 | 188 |
| Dri-Bottoms Supreme | 4 | Paragon Trade Brands | USA | 0.44 | 43 | 19 | 32.4 | 66 | 0.0* | 4.6 | 188 |

*Because the absorbent matter entirely absorbed the liquid, the liquid did not flow out.

As is shown in Table 4 above, as to all the commercially available diapers as tested above, the concentration absorption index was less than 35, and the absorption amount in a state of lying face down was small.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A process for producing an absorbent article having an absorbent layer, a liquid-permeable surface sheet, and a liquid-impermeable back sheet, wherein the absorbent layer includes an absorbent matter having a water-absorbent resin and a fibrous material in a ratio by weight, "α," of the water-absorbent resin to the total of the water-absorbent resin and the fibrous material, wherein the ratio by weight "α" is at least 0.4, with the process comprising the step of using as the water-absorbent resin a water-absorbent resin which has a concentration absorption index of 35 or more as shown by the following equation (1):

$$A(1-\alpha)+B\alpha \qquad (1)$$

wherein A (g/g) is an absorption capacity of the resin under no load, and

B (g/g) is an absorption capacity of the resin under a load.

2. A process according to claim 1, wherein the content of the water-absorbent resin per sheet of the absorbent article is 8 g or more.

3. A process according to claim 1, wherein the ratio by weight "α" is in the range of 0.6 to 0.9.

4. A process according to claim 1, wherein the fibrous material is a hydrophilic fiber, and the absorbent matter includes a homogeneous mixture of the water-absorbent resin and the hydrophilic fiber.

5. A process according to claim 1, wherein the absorbent matter has a second-time liquid permeation speed of γ (1−α) (g/min) or less, wherein γ (g/min) is a liquid permeation speed of the fibrous material.

6. A process according to claim 1, wherein the absorbent matter has a third-time liquid permeation speed of 0.05 (g/min) or more.

7. An absorbent article, comprising an absorbent layer, a liquid-permeable surface sheet, and a liquid-impermeable back sheet, wherein the absorbent layer includes an absorbent matter having a water-absorbent resin and a fibrous material in a ratio by weight, "α," of the water-absorbent resin to the total of the water-absorbent resin and the fibrous material, wherein the ratio by weight "α" is at least 0.4, and wherein the water-absorbent resin has a concentration absorption index of 35 or more as shown by the following equation (1):

$$A(1-\alpha)+B\alpha \qquad (1)$$

wherein A (g/g) is an absorption capacity of the resin under no load, and

B (g/g) is an absorption capacity of the resin under a load.

8. An absorbent article according to claim 7, wherein the content of the water-absorbent resin per sheet of the absorbent article is 8 g or more.

9. An absorbent article according to claim 7, wherein the ratio by weight "α" is in the range of 0.6 to 0.9.

10. An absorbent article according to claim 7, wherein the fibrous material is a hydrophilic fiber, and the absorbent matter includes a homogeneous mixture of the water-absorbent resin and the hydrophilic fiber.

11. An absorbent article according to claim 7, wherein the absorbent matter has a second-time liquid permeation speed of γ (1−α) (g/min) or less, wherein γ (g/min) is a liquid permeation speed of the fibrous material.

12. An absorbent article according to claim 7, wherein the absorbent matter has a third-time liquid permeation speed of 0.05 (g/min) or more.

* * * * *